United States Patent [19]
Larzul

[11] Patent Number: 5,176,203
[45] Date of Patent: Jan. 5, 1993

[54] APPARATUS FOR REPEATED AUTOMATIC EXECUTION OF A THERMAL CYCLE FOR TREATMENT OF SAMPLES

[75] Inventor: M. Daniel Larzul, Savigny sur Orge, France

[73] Assignee: Societe de Conseils de Recherches et d'Applications Scientifiques, France

[21] Appl. No.: 560,107

[22] Filed: Jul. 31, 1990

[30] Foreign Application Priority Data

Aug. 5, 1989 [GB] United Kingdom ............... 8917963

[51] Int. Cl.⁵ .................... F25B 29/00; C12M 1/38
[52] U.S. Cl. ........................ 165/61; 417/50; 422/189; 422/198; 435/316; 435/290
[58] Field of Search ............ 435/288, 290, 316; 436/173, 147, 157; 165/61, 63, 64, 65, 120; 417/50; 73/863.11; 422/198, 199

[56] References Cited

U.S. PATENT DOCUMENTS

| | | | |
|---|---|---|---|
| 2,698,127 | 12/1954 | Bowlus | 417/50 |
| 2,863,922 | 12/1958 | Sturzenegger | 422/198 |
| 2,964,532 | 12/1960 | Klenke, Jr. | 422/199 |
| 3,108,060 | 10/1963 | Matthews, II | 422/198 |
| 3,354,642 | 11/1967 | Soder | 417/50 |
| 3,411,884 | 11/1968 | Thayer | 422/198 |
| 3,488,152 | 1/1970 | Kuehl | 422/198 |
| 3,574,485 | 4/1971 | Herman, Jr. | 417/50 |
| 3,738,815 | 6/1973 | Pawloski et al. | 422/198 |
| 3,933,200 | 1/1976 | Cunningham | 165/64 |
| 4,015,943 | 4/1977 | Wulf et al. | 422/189 |
| 4,095,952 | 6/1978 | Schmidt et al. | 422/189 |
| 4,113,435 | 9/1978 | Lagow et al. | 165/63 |
| 4,137,966 | 2/1979 | Ulrich et al. | 165/61 |
| 4,181,576 | 1/1980 | Malick | 435/316 |
| 4,247,518 | 1/1981 | Charlet et al. | 422/142 |
| 4,276,174 | 6/1981 | Breider et al. | 435/316 |
| 4,544,025 | 10/1985 | Aldrich et al. | 165/61 |
| 4,603,243 | 7/1986 | Septfons et al. | 165/61 |
| 4,865,987 | 9/1989 | Seppo | 435/290 |
| 5,038,852 | 8/1991 | Johnson et al. | 165/12 |

FOREIGN PATENT DOCUMENTS

| | | | |
|---|---|---|---|
| 596284 | 4/1960 | Canada | 417/50 |
| 174555 | 7/1988 | Japan | 417/50 |
| 26360 | 1/1989 | Japan | 417/50 |
| 182516 | 11/1966 | U.S.S.R. | 417/50 |
| 823110 | 11/1959 | United Kingdom | 417/50 |

*Primary Examiner*—John K. Ford
*Assistant Examiner*—L. R. Leo
*Attorney, Agent, or Firm*—Lucas & Just

[57] ABSTRACT

Apparatus for repeated automatic execution of a thermal cycle for the treatment of a sample, especially a biological sample, comprises means (6) defining a pathway which is physically closed throughout the treatment and within which the sample is resident throughout the treatment. Means (3, 4, 11, 12) are provided to move the sample between different positions along the pathway and (7, 15, 16) to heat or cool the sample as a function of its position within the pathway. Preferably the pathway is a capillary tube, which may be in spiral, closed loop or linear form. Heating and cooling means are provided by thermostated zones which may provide a continuous thermal gradient regular or irregular, or be in a discontinuous arrangement. The preferred means of moving the samples is magnetic.

18 Claims, 3 Drawing Sheets

APPARATUS FOR REPEATED AUTOMATIC EXECUTION OF A THERMAL CYCLE FOR TREATMENT OF SAMPLES

The invention relates to apparatus for repeated automatic execution of a thermal cycle for the treatment of biological samples.

Such an apparatus has numerous applications in biology in general and microbiology in particular. In the latter field, the necessity of treating a biological sample at different temperatures is generally dictated by two basic biological characteristics. First, the biological activity of an enzyme is greatly dependent on the temperature. In general, each enzyme has an optimum operating temperature and its activity decreases regularly if one moves away from this temperature. Curves showing the variations in biological activity as a function of temperature may thus be obtained and represent an important characteristic of each enzyme. Secondly, the reaction of molecular hybridisation between two sequences of nucleic acids is directly connected to the temperature. This hybridisation based on the complementarity of the bases between two sequences may occur between two molecules of deoxyribonucleic acid (DNA), between two molecules of ribonucleic acid (RNA) or between one molecule of DNA and one molecule of RNA. Molecular hybridisation enables one to produce either pairing by hydrogenous connection between two distinct molecules or intermolecular pairing between two complementary sequences. In the latter case, there is the formation of a so-called secondary structure of DNA or RNA molecules. The effect of temperature on the hybridisation reaction is essential and each sequence of DNA (or RNA) is defined by its Tm, i.e.: the temperature at which 50% of the sequences are paired to complementary sequences. The Tm of a precise sequence is evaluated experimentally following the hyperchromicity at 260 nm by spectro-photometry, which accompanies the unpairing (or denaturing) of two complementary sequences of DNA. The whole of the DNA sequences are in the single strand form at high temperature (100° C.) and the double strand form at low temperature (10°-20° C.).

The Tm of a DNA sequence depends essentially on the following two parameters: the basic sequence and ionic force of the medium. The Tm usually found varies between 20° and 85° C. Thus, the great majority of molecular reactions may be produced in perfectly defined and controlled thermal conditions. Certain of these reactions require the successive use of different temperatures and may be effected in the apparatus described in this invention. This particularly concerns hydrolysis using restriction enzymes, enzyme modification reactions for DNA, cascade enzyme reactions, the isolation of repetitive families of sequences for DNA and the amplification by 'polymerase chain reaction'. These applications will now be discussed in greater detail.

Hydrolysis of DNA by restriction enzymes

A restriction enzyme enables one to cut a hybridisation duplex DNA/DNA at a very specific place defined by its sequence. For the great majority of these enzymes, the temperature of maximum activity is 37° C. The incubation time of DNA with the enzyme at 37° C. varies between 30 min and several hours. Thus, a simple method of inactivating the enzyme consists of incubating the sample for several minutes at 100° C., a temperature at which the enzyme is irreversibly denatured. This treatment is equally effective in DNA denaturation which returns to its double strand form if it is subjected to progressive reduction of the temperature from 110° C. to 20° C. Sudden cooling of the sample does not enable one to achieve correct renaturing of the DNA. Progressive cooling in particular may proceed by stages.

Generalisation of the set of enzyme treatments of DNA and RNA

This method applied for restriction enzymes may be adapted for the treatment of many enzymes, for example:
polynucleotic kinases
ligases
the terminal deoxynucleotidyl transferase
DNA and RNA polymerases
endonucleases and exonucleases

Cascade enzyme treatment

Many successive enzyme treatments may be necessary to obtain one or more defined DNA sequences. A change of the reaction medium is generally necessary between two enzyme reactions.

Isolation of repetitive families of DNA sequences

DNA sequences in large numbers exist in complex genomes (human genome = $3.5 \times 10^9$ basic pairs). It is possible to distinguish different repetitive families of sequences as a function of the number of copies of sequences per genome. Thus, DNA genomes totally denatured thermally are restored in stages and in a selective manner. The very repetitive sequences are restored first (family 1), then the medium repetitive sequences (family 2), then the hardly repetitive sequences (family 3) and finally, the unique sequences (family 4). It is thus possible to isolate these different families by passing the sample into affinity columns of the hydroxy-apatite type, enabling one to separate single strand DNA molecules from double strand DNA molecules. They are passed into the columns at a precise temperature during stage by stage cooling of the sample. The temperature of the first column is around the melting temperature (Tm) of family 1 sequences. In these conditions, sequences of family 1 can be separated from sequences of families 2, 3 and 4. The same process is applied for separation of families 2, 3 and 4. The apparatus described in this invention is particularly well adapted to carry out this thermal sequence.

Amplification of the number of DNA sequences by 'Polymerase chain reaction' (PCR)

This technique enables one specifically to amplify the number of copies of a double strand DNA sequence. The principle of PCR (R. K. Saiki et al, Science, 230, 1985, 1350-1354) is to use the activity of the DNA polymerase DNA dependent initiating the synthesis starting from oligonucleotidic initial material (P1 and P2) added in the reaction medium. An amplification cycle consists of three successive stages:
Stage 1
 Denaturing of the DNA with double strands at 90°-100° C.
Stage 2
 Hybridisation of oligonucleotidic primers (15-35 nucleotides) P1 and P2 on the target sequences.

P1 hybridizes with the (+) strand and P2 hybridizes with the (−) strand. This stage is carried out at a temperature close to the mean of the Tm's of P1 and P2.

Stage 3

Synthesis of the complementary DNA strand by extension of the primers P1 and P2, thanks to the activity of a DNA polymerase. This stage takes place close to the optimum operating temperature of the enzyme, either at 37° C. for the Klenow fragment or at 72° C. for the Taq polymerase.

Thus, after an amplification cycle, the number of sequences completed by P1 and P2 is multiplied by 2, multiplied by 4 after 2 cycles, by 8 after 3 cycles, by 1024 after 10 cycles and by 1,048,576 after 20 cycles. Generally, the rate of amplification after n cycles is $2^n$. A cycle of amplification thus consists of 3 successive thermal stages and one complete PCR reaction requires about 10 to 60 cycles. Each thermal stage generally lasts from 1 to 5 mins. Automation of such a technique thus represents considerable progress.

The invention provides apparatus for repeated automatic execution of a thermal cycle for the treatment of a sample, the apparatus comprising means defining a pathway which is physically closed throughout the treatment and within which the sample is resident throughout the treatment, means for moving the sample between different positions along the pathway, and means for heating and cooling the sample as a function of its position within the pathway.

The means defining the pathway preferably comprises a capillary tube. This may be of a semi-rigid material such as plastics material, and may be of small diameter, from approximately 0.1 mm to approximately 4 mm, preferably from 1 mm to 3 mm. Such a small internal cross-section ensures a large heat exchange surface to volume ratio, and therefore enables rapid temperature variations, particularly as compared to a sample in a conventional 0.5 to 1.5 ml tube. The sample treated in the apparatus of the invention is usually of from 1 to 50 microlitres.

Various spatial arrangements of the capillary tube are envisaged. It may, for instance, be in a spiral form, in a closed loop form or in linear form. Each turn of the spiral, each turn of the closed loop or each passage of the length of linear capillary tube represents one thermal cycle, within which the sample passes through two or more thermostated zones, at different temperatures from 4° C. to 150° C. Further thermal cycles, up to 100, comprise the next turn of spiral, a further turn within the closed loop, or the return of the sample in reverse direction along the length of the linear capillary tube.

The thermostated zones may be arranged on a discontinuous system or on a continuous system. In a discontinuous system, the zones are separated by a physical barrier, crossed only by the capillary tube. Each zone has an autonomous heating or cooling system. The inter-zone barrier isolates each zone from the thermal effect of the adjacent zone(s). In a continuous system there is no physical barrier. The capillary tube crosses a continuous and directional thermal gradient, which may be created in a liquid, gaseous or solid medium. A change of medium gives the possibility of a continuous but irregular thermal gradient.

The rate of movement of the sample through the capillary tube has a profound effect on the treatment. If the sample moves very slowly through a zone, its temperature will approach or reach the zone temperature. The sample may even be stopped within a given zone for a predetermined period, stabilising its temperature at that of the zone. On the other hand, if the sample moves rapidly through a zone, the thermal effect of that zone on the sample may be minimised or suppressed.

The movement of the sample in the capillary tube may be obtained in different ways:
by at least one peristaltic pump acting on a capillary zone having a flexible wall;
by displacement in a magnetic system consisting of two parts:
  of a magnet and of a party responding to the effect of the magnet (metal part or second magnet);
  One of the parts is solidly connected to a mechanical drive system, enabling it to rotate (circular system) or to be displaced (linear system). The other part is situated inside the capillary and is solidly connected to the sample. This part may consist of at least one solid particle (globule, cylinder, suspension of microparticles in a liquid etc) or at least of one liquid particle.
by the effect of at least one pump acting on a gas:
by passive capillary action;
by the effect of thermal pumping created by the proximity of gaseous masses at different temperatures inside the capillary.

The movement of the sample may also be obtained by a combination of two or more of these processes. The movement of the sample may be under microprocessor control.

The apparatus of the invention uses a semi-closed system, represented by the capillary, reducing the risk of molecular contamination during treatment of the biological sample.

The invention is illustrated with reference to the drawings, of which:

Figure 1A:
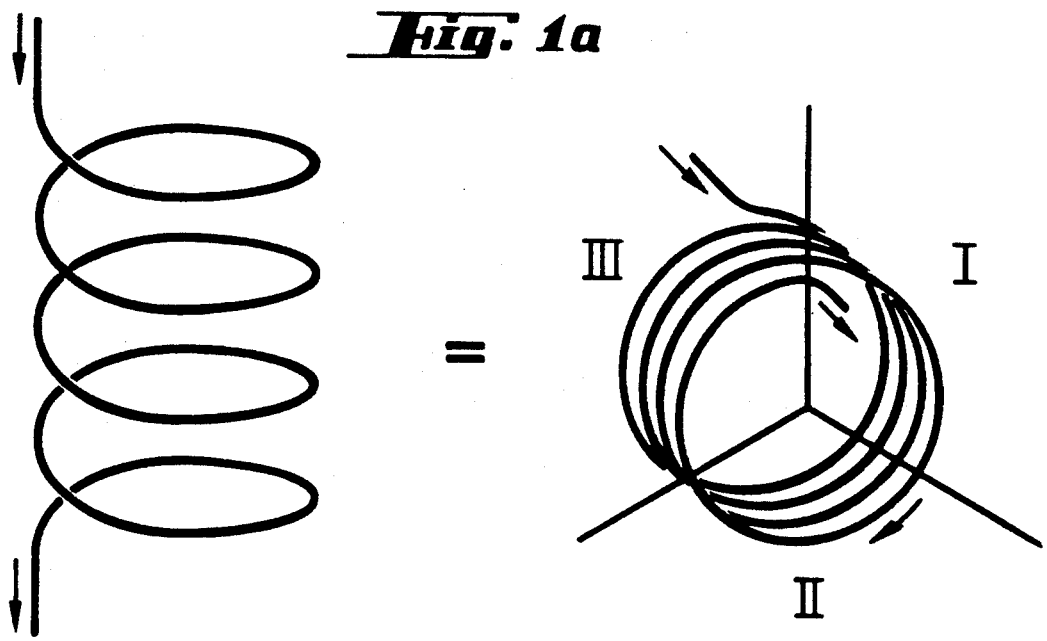
FIGS. 1a, 1b and 1c are schematic diagrams of the apparatus of the invention, showing the helical, closed loop and linear arrangements respectively of the capillary tube.
Figure 1B:
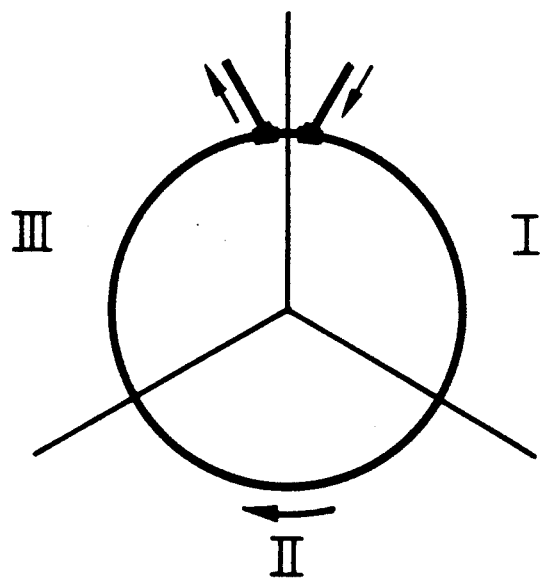
Figure 1C:
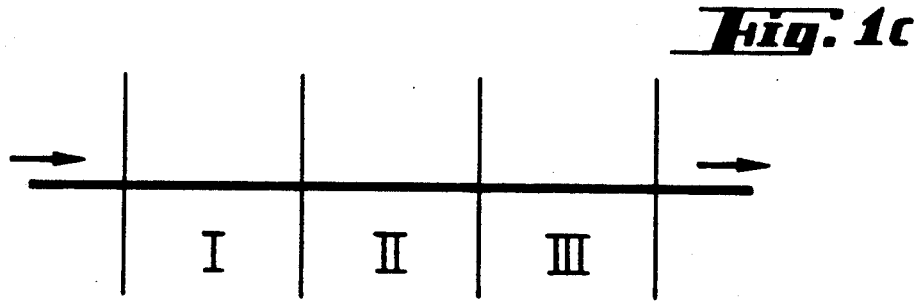

Referring first to FIGS. 1a-c, three schematic diagrams are presented. In each, there are three thermostated zones I, II and III through which the biological sample in the capillary tube passes in a single thermal cycle. The thermostatic zones I, II and III could be replaced by a continuous or discontinuous thermal gradient. In the spiral form of FIG. 1a, there are as many loops as there are thermal cycles to be performed. In the closed loop form of FIG. 1b, there is just one loop and each thermal cycle consists of one circuit of the closed loop by the biological sample. In the linear form of FIG. 1c the first thermal cycle is completed by the passage of the sample from left to right, that is through thermostated zone I, thermostated zone II and thermostated zone III in succession. The second thermal cycle is completed by the return passage of the sample from right to left, that is through thermostated zone III, thermostated zone II and thermostated zone I in succession. Each odd numbered cycle follows the pattern of the first and each even numbered cycle follows the pattern of the second. It is noted that the sample essentially passes through the thermostated zone II in each direction, so producing a succession of thermostated zones I, II, III, III, II, I, I, II, III, III, II, I . . . However, the passage through thermostated zone II on even cycles can be completed quickly to minimise its effect, and the delay times in zones I and III adjusted to achieve the same I,II,III,I,II,III,I,II,III . . . effect as in the spiral and closed loop arrangements.

Figure 2:
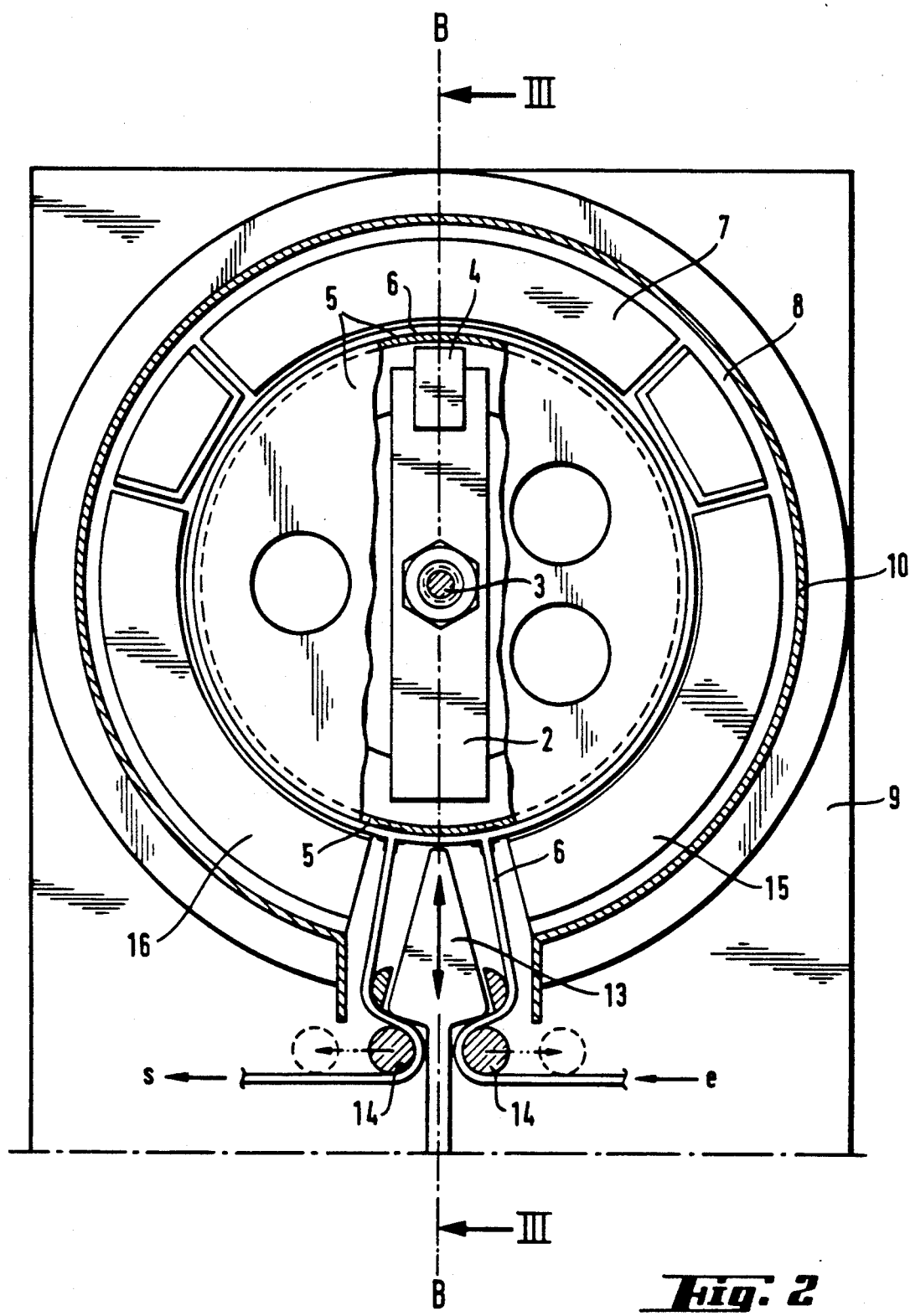
FIG. 2 is a cross-sectional view according to the section line II—II of FIG. 3 of an apparatus according to the invention in which the capillary tube is of closed loop form.
Figure 3:
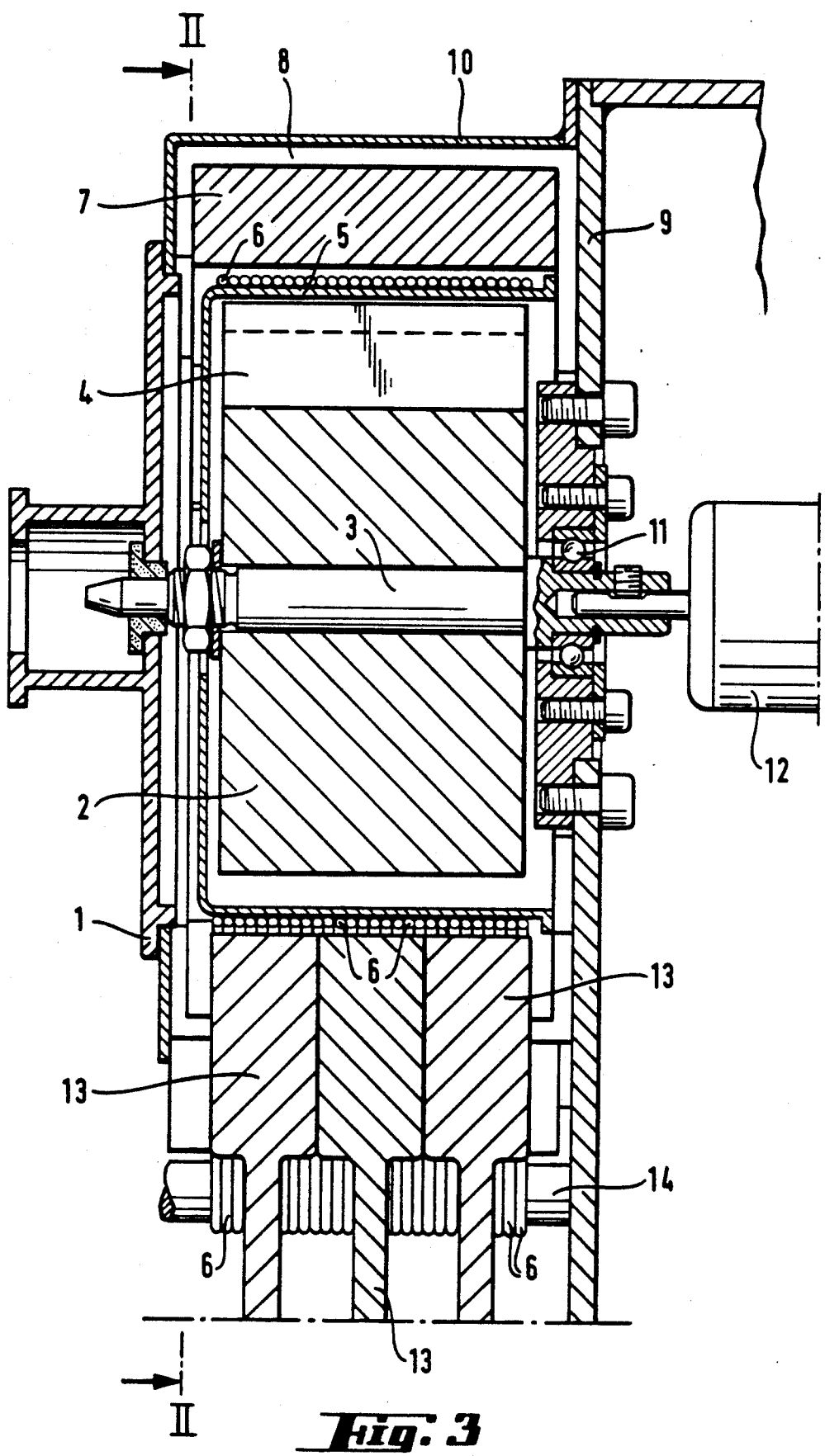
FIG. 3 is a sectional view of the apparatus of FIG. 2, taken on the section line II—II of FIG. 2.

Referring now to FIGS. 2 and 3, the apparatus illustrated shows a closed loop form of the apparatus of the invention, with a magnetic displacement system for the biological sample and a discontinuous system of thermostated zones.

The apparatus is provided with a capillary tube 6 in the form of a closed loop. The capillary tube 6 is provided with a branch e for entry of the sample to be treated, and with a branch s for removal of the sample after treatment.

A key 13 is movable along the axis B—B between a radially inward position, in which the capillary tube 6 is pressed against a wall 5, and a radially outward position, in which the capillary branches e and s are pressed against the elements 14. In the radially inward position, the capillary loop 6 is interrupted and the branches e and s are open for entry and removal of the sample. In the radially outward position the branches e and s are closed, and the sample is free to continue cycling around the closed loop capillary 6. The means for moving the key 13 are external to the apparatus described, and are not shown in the drawings.

For movement of the sample around the closed loop capillary 6, a magnetic system is used. This comprises a magnet 4 carried on an arm 2 fast with a drive shaft 3. The drive shaft 3 is journalled at 11 and powered by a motor 12. Responsive to the effect of the magnet 4 is a party formed by metallic micro-globules in suspension in mineral oil. This party is in the capillary tube 6 in abutment with the sample.

During one turn of the sample around the closed loop capillary 6, the sample passes close to thermostatic compartments 7, 15 and 16. The sample is under the thermal influence of the compartment in regard of which it finds itself for the time being. Each of these compartments 7, 15 and 16 is thermally regulated at a temperature between 4° C. and 150° C. The compartments are isolated from a brace 10, carried by a mounting plate 9, by an adjustable spacing 8.

The motor 12 is under the control of a programmable microprocessor, allowing various parameters associated with the movement of the sample to be fixed. These parameters include the total number of cycles to which the sample is subjected, the speed of movement of the samples, and the number, position and duration of stops of the sample during each cycle. The microprocessor is interfaced with a thermocouple which continuously measures the actual temperature of the sample in the capillary tube 6. The various parameters of movement of the sample can thus be varied as a function of the measure temperature, under the programmed control of the microprocessor. The microprocessor under programmed control may also govern the movement of the keys 13, the temperature in the compartments 7, 15 and 16 and external apparatus, such as a peristaltic pump, governing the movement of the sample in the entry and exit branches. FIG. 3 shows three independent keys 13, each associated with a capillary tube 6.

I claim:

1. Apparatus for the treatment of biological and microbiological samples comprising:

(a) a pathway which is physically closed throughout the treatment;
    (b) means for introducing one of said biological or microbiological samples to the pathway prior to the commencement of treatment and for removing said sample subsequent to the completion of treatment;
    (c) means for physically closing the pathway during treatment so that nothing can be added thereto or withdrawn therefrom;
    (d) a plurality of thermal means positioned along the pathway for heating or cooling of said sample, said thermal means providing treatment of said sample at a temperature of from 4° C. to 150° C.; and
    (e) means for automatically and repeatedly, through a plurality of cycles, moving said sample between said different thermal positions along the pathway.

2. Apparatus according to claim 1 in which the pathway comprises a capillary tube.

3. Apparatus according to claim 2 in which the capillary tube is of semi-rigid plastics material.

4. Apparatus according to claim 2 in which the capillary tube has an internal diameter of from 0.1 to 4 mm.

5. Apparatus according to claim 1 in which the pathway is a spiral pathway.

6. Apparatus according to claim 1 in which the pathway is a loop.

7. Apparatus according to claim 1 in which the pathway is a linear pathway.

8. Apparatus according to claim 1 in which the means for heating or cooling the sample comprises two or more thermostated zones through which the pathway passes.

9. Apparatus according to claim 8 in which the thermostated zones are arranged discontinuously, each being separated from the next by a physical barrier crossed only by the pathway and each being provided with an autonomous heating or cooling system.

10. Apparatus according to claim 8 in which the thermostated zones are arranged continuously along the pathway to provide a continuous and directional thermal gradient.

11. Apparatus according to claim 10 in which the thermal gradient is irregular.

12. Apparatus according to claim 1 in which the means for moving the sample comprises magnetic means including magnetic party within the pathway adjacent to the sample and an external magnet acting on the magnetic party to move it and hence the sample.

13. Apparatus according to claim 12 in which the magnetic party is a solid magnet or a suspension of magnetic microparticles in a liquid immiscible with the sample.

14. Apparatus according to claim 1 in which the means for moving the sample comprises a pump acting on a gas.

15. Apparatus according to claim 1 in which the means for moving the sample comprises the effect of thermal pumping created by the proximity of gaseous masses at different temperatures within the pathway.

16. Apparatus according to claim 2 in which the means for moving the sample comprises passive capillary action.

17. Apparatus according to claim 1 in which the means for moving the sample comprises a peristaltic pump.

18. Apparatus for the treatment of biological and microbiological samples comprising:

(a) a loop pathway which is physically closed throughout the treatment;
(b) means for introducing one of said biological or microbiological samples to the loop pathway prior to the commencement of treatment and for removing said sample subsequent to the completion of treatment;
(c) means for physically closing the loop pathway during treatment so that nothing can be added thereto or withdrawn therefrom;
(d) a plurality of thermal means positioned along the loop pathway for heating or cooling of said sample, said thermal means providing treatment of said sample at a temperature of from 4° C. to 150° C.; and
(e) means for automatically and repeatedly, through a plurality of cycles, moving said sample between said different thermal positions along the loop pathway.

* * * * *